United States Patent [19]

Houck et al.

[11] Patent Number: 4,696,925

[45] Date of Patent: Sep. 29, 1987

[54] CHOLECYSTOKININ ANTAGONIST COMPOUNDS

[75] Inventors: David R. Houck, Fanwood; Edward S. Inamine, Rahway; Michael A. Goetz, Fanwood, all of N.J.

[73] Assignee: Merck & Co., Inc., Rahway, N.J.

[21] Appl. No.: 695,113

[22] Filed: Jan. 25, 1985

[51] Int. Cl.[4] .................. A61K 31/55; C07D 519/00; C12P 17/18; C12R 1/66

[52] U.S. Cl. .................. 514/219; 540/492; 540/494; 435/119; 435/913; 435/118

[58] Field of Search ................ 540/492, 494; 514/219

[56] References Cited

U.S. PATENT DOCUMENTS 4,530,790 7/1985 Monahan et al. .................... 540/494
4,559,339 12/1985 Bock et al. .......................... 540/494

FOREIGN PATENT DOCUMENTS 0116150 8/1984 European Pat. Off. .

OTHER PUBLICATIONS

Mutt & Jorpes, Biochem. J. 125 57P (1971).
A. J. Williams, Biomed. Res. 3 (1982).
A. J. Prange et al., Peptides in the Central Nervous System, Ann. Repts. Med Chem. 17 31, 33 (1982).
J. E. Morely, Life Sci. 30 479 (1982).

Primary Examiner—Robert T. Bond
Attorney, Agent, or Firm—Samuel B. Abrams; Hesna J. Pfeiffer

[57] ABSTRACT

Products of *Aspergillus alliaceus* fermentation having cholecystokinin (CCK) antagonist activity, their preparation and use are disclosed.

9 Claims, 4 Drawing Figures

Fig. 1
COMPOUND 500

Fig. 2
COMPOUND 654

Fig. 3
COMPOUND 655

Fig. 4
COMPOUND 656

CHOLECYSTOKININ ANTAGONIST COMPOUNDS

BACKGROUND OF THE INVENTION

This invention concerns cholecystokinin antagonists prepared by fermentation of *Aspergillus alliaceus*.

Cholecystokinin (CCK) is a neuropeptide (See: Mutt and Jorpes, *Biochem. J.* 125 678 (1971)) which exists in both gastrointestinal tissue and the central nervous system. CCK is believed to play an important role in appetite regulation and CCK may be a physiological satiety hormone. CCK reportedly co-exists with dopamine in certain mid-brain neurons and thus may additionally play a role in the functioning of dopaminergic systems in the brain, as well as, serving as a neurotransmitter in its own right. (See: A. J. Prange et al., "Peptides in the Central Nervous System", *Ann. Repts. Med Chem.* 17 31, 33 (1982), Mutt et al., *Biochem. J.* 125, 678 (1971), J. A. Williams, *Biomed. Res.* 3 107 (1982) and J. E. Morley, *Life Sci.* 30 479 (1982). CCK antagonists are useful in the treatment and prevention of disorders of the gastrointestinal, central nervous and appetite regulatory sytems of animals, especially humans. CCK antagonists of the formulae:

prepared by a particular fermentation of *Aspergillus alliaceus* are disclosed in European Patent Application No. 0,116,150 published August 22, 1984.

Novel CCK antagonists have been prepared by fermentation of *Aspergillus alliaceus* in a modified medium.

SUMMARY OF THE INVENTION

CCK antagonist compounds, their preparation by fermentation and their use.

REFERENCE TO DRAWINGS

An embodiment of this invention is a compound of the formula:

-continued or and pharmaceutically acceptable salts thereof wherein X is C or N and $R_1$, $R_2$ and $R_3$ are independently selected from H, F, and $CH_3$ and $R_4$ is selected from cyclopentyl, cyclohexyl, phenyl, $(CH_3)_2CH-CH_2-$, $(CF_3)(CH_3)CH-CH_2-$, $CH_2=C(CH_3)-CH_2-$, $CH_2=CH-CH_2-$, $CH_3-CH_2-CH_2-$, $CH_3-CH_2-(CH_3)CH-$, $CH_3-(CH_2)_3-$, $CH_3-S-(CH_2)_2-$, and $CH_3-CH_2-S-(CH_2)_2-$ such that $R_1$, $R_2$ and $R_3$ are all H only when $R_4$ is other than $(CH_3)_2CH-CH_2-$.

The pharmaceutically acceptable salts include the acid addition and quarternary ammonium salts. Representative acid addition salts are $C_1-C_{12}$alkanoates, e.g. acetate, butyrate, dodecanoate, octonoate, pentanoate, pivaloate, fumarate, maleate, and hydrogen maleate; nitrate, sulfate, phosphate, halide; isethionate; pamoate and the like. These salts are prepared using conventional procedures.

The compounds of the present invention are produced by the controlled aerobic fermentation of a strain of *Aspergillus alliaceus*, Thom and Church, preferably, ATCC No. 20655 or ATCC No. 20656. A description of *Aspergillus alliaceus* is found in said published European patent application No. 0 116 150 and to the extent necessary is incorporated herein by reference.

The general fermentation process described in said European patent application is the basic procedure used in the preparation of the present compounds. However, the process is modified by varying the amino acids in the fermentation medium so as to obtain the compounds of the present invention.

The ability of the compounds of Formulae I, II and III to antagonize CCK makes these compounds useful as pharmaceutical agents. These compounds will be especially useful in the treatment and prevention of disease states wherein CCK may be involved, for example, gastrointestinal disorders such as irritable bowel syndrome, ulcers, acute pancreatis, motility disorders, central nervous system disorders caused by CCK's interaction with dopamine such as neuroleptic disorders, tardive dyskinesia, Parkinson's disease, psychosis or Gilles de la Tourette Syndrome, and disorders of the appetite regulatory systems.

A compound of Formulae I, II or III and its minor related compounds or a pharmaceutically acceptable salt thereof, can be administered to a human subject either alone, or preferably, in combination with pharmaceutically acceptable carriers or diluents, in a pharmaceutical composition, according to standard pharmaceutical practice. The compound can be administered orally or parenterally. Parenteral administration includes intravenous, intramuscular, intraperitoneal, subcutaneous and topical administration.

For oral use of an antagonist of CCK of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When the compound of Formula I (II or III) and its minor related compounds or a salt thereof is used as an antagonist of CCK in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 1 mg to about 1500 mg and preferably 10 mg to 500 mg in a single or divided doses. On the other hand, it may be necessary to use dosages outside these limits in some cases.

GENERAL FERMENTATION

Compounds of formula I, II or III can be prepared by controlled aerobic fermentation of the microorganism *Aspergillus alliaceus* Thom and Church, ATCC No. 20655 or ATCC No. 20656. The fermentation should be conducted at a temperature range of from about 20° to 37° C., preferably at about 28° C. Generally, the composition of the assimilable nutrient medium may be varied over a wide range. The essential nutrient ingredients are a carbon source and a nitrogen source. Other essential nutrients are provided via mineral salts such as the chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; glucose, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysates (e.g., casein, yeast, etc.) and industrial by-products such as lard water and distillers solubles.

The maximum yield of the compound of Formulae I, II or III can be achieved within about 24 to 200 hours usually in about 96–144 hours, of fermentation fermentation may be provided from vegetative growth in a medium which supports rapid growth of the microorganism, or directly from spores.

Following fermentation, the accumulated compound of Formulae I, II or III may be recovered from the broth by conventional chromatographic means.

The fermentation broth is filtered to separate mycelia from liquid supernatant. These are extracted as follows:
  A. The supernatant is shaken with an equal volume of a moderately polar solvent, immiscible in water such as; chloroform, ethyl acetate, methyl ethyl ketone, and the like. The layers are allowed to settle; the organic phase contains all of the compound of Formula I, II or III initially located within the supernatant.
  B. The mycelia are stirred vigorously (homogenized) with several volumes of acetone, ethyl acetate, methyl ethyl ketone or the like. These solvents will dissolve most of the compound of Formula I located within the mycelia.

The combined mycelial and supernatant organic extracts are then concentrated to a small volume under reduced pressure. The resultant mass is subjected to a series of solvent partioning and washing steps. Solvents of choice include petroleum ether, hexane, ether, methylene chloride, methanol and similar solvents.

Adsorption and partition chromatographies, gel filtration, reversed-phase liquid chromatography and the like may be used, in conjunction with eluents of proper polarity and solubilizing characteristics to afford the compound of Formula I, II or III.

A number of different nutrient media may be employed in the fermentation of *Aspergillus alliaceus* Thom and Church, ATCC No. 20655 and ATCC No. 20656. Variation of the medium or the microorganism will vary the yield of the compound of Formula I and/or its rate of production. Variation of the medium or the microorganism may also increase or decrease the type and amount of the several minor related compounds present in the broth.

General Procedure for Detection, Isolation and Purification of the Formula I, II or III Compound The resting cell preparation is extracted with vigorous shaking with an equal volume of an organic solvent which is immiscible with water such as toluene, methylene chloride, ethyl acetate, butanol, methylethyl ketone and the like, ethyl acetate being the preferred solvent. After shaking, the two phases are allowed to separate and the organic phase is collected. The solvent is then removed by evaporation under reduced pressure with slight heating to afford a solid or oily residue; this is redissolved in the smallest amount possible of a solvent compatible with water such as acetone, methanol, ethanol and the like, with methanol being the preferred solvent.

An aliquot of this solution is used for analysis by a chromatographic method such as normal-phase or reverse-phase thin layer chromatography (TLC) or high performance liquid chromatography (HPLC). Reverse-phase HPLC is usually the method of choice; this is run on a Zorbax octadecylsilane bonded phase ($C_{18}$) column with an isocratic or gradient elution employing mixtures of water and an organic solvent such as acetonitrile, methanol or tetrahydrofuran. This analytical run is of advantage in detecting the chemical entities produced by the resting-cell fermentation [detection is carried out by ultraviolet (UV) absorption at 254 nm], in determining the number of these compounds and in establishing the proper conditions for their preparative-scale purification.

Upon establishment of the separation parameters, the remainder of the solution is fractionated on a preparative size reverse-phase Zorbax $C_{18}$ column, again with an isocratic or gradient elution with mixtures of water and a solvent such as acetonitrile, methanol or tetrahydrofuran.

The eluent from this column is collected in tubes; fractions containing the compounds of interest are determined by a chromatographic analytical procedure as described above; this analytical run is also of use in determining the purity of the isolated compounds. The appropriate fractions are combined, the solvent is removed under vacuum with slight heating and the solid residue obtained is characterized by the proper spectroscopic means which include UV absorption, infra-red absorption, mass spectrometry and nuclear magnetic resonance.

General Conditions for the Analytical Runs by Reverse-Phase HPLC

Zorbax $C_{18}$ analytical column, 4.6 mm 1D×25 cm length, 7 μm bonded particles, maintained at 40° C. with a constant temperature water bath; flow rate of eluent 2 ml/min; detection of compounds by UV absorption at 254 nm, 0.16 Absorption Units Full Scale; eluents ranging from 40% water, 60% acetonitrile to 70% water, 30% acetonitrile.

General Conditions for the Preparative Scale Purifications by Reverse-Phase HPLC Zorbax $C_{18}$ analytical column, 1 inch×25 cm, 7 μm bonded particles, maintained at 40° C. with a constant temperature water bath; flow rate of eluent 10 ml/min; detection of compounds by UV absorption at 254 nm, 2.56 Absorption Units Full Scale; eluents ranging from 40% water, 60% acetonitrile to 70% water, 30% acetonitrile.

Specific Fermentation

A lyophile tube, *Aspergillus alliaceus*, ATTC 20738 a natural isolate of ATCC 20656, was asceptically opened and grown on agar slants containing yeast malt extract. The spores from the agar slants were used to inoculate the defined seed medium which was in turn used to inoculate a defined production medium. The seed culture was grown in a 3-baffle 250 ml flask on a rotary shaker for 28 hours at 27° C. The production cultures were grown under the same conditions in an unbaffled flask for 48 to 96 hours. The defined medium consisted of L-glutamate, glycerol, ammonia, phosphate, magnesium, zinc, and iron. After 48 to 60 hours of growth, the cells from the production cultures could be removed from the medium by centrifugation, washed with buffer and then used for the biosynthesis of formula I, II or III compounds under defined condition.

Washed cells were usually combined with the amino acid precursors to I, II or III and then incubated on a rotary shaker for 24 to 48 hours. For maximum production of I, II or III the washed cells were incubated with appropriate amino acids. Compound I, II or III was quantitatively extracted from the incubations into two volumes of ethyl acetate. After evaporating the ethyl acetate and redissolving the residue in methanol, I, II or III could be separated by reverse phase HPLC. The HPLC procedure was used to quantitate I, II or III. Isolation of the compound I, II or III was usually accomplished by silica gel column chromatography, thin layer chromatography (TLC) on silica gel, followed by reverse phase high performance liquid chromatography (HPLC). Structural identification of I, II or III was performed by high resolution mass spectrometry and proton nuclear magnetic resonance spectroscopy (NMR).

| Fermentation Media | | | |
|---|---|---|---|
| Medium A | Slant Medium: | yeast malt extract | 4.0 g |
| | | malt extract | 4.0 g |
| | | dextrose | 10.0 g |
| | | agar | 20.0 g |
| | | 1000 ml distilled water pH | 7.0 |
| Medium B | Seed Medium: | L-glutamate | 5.0 g |
| | | lecithin (Centrolex P) | 1.0 g |
| | | glycerol | 15.0 g |
| | | NH$_4$Cl | 2.0 g |
| | | K$_2$HPO$_4$ | 2.0 g |
| | | KCl | 0.5 g |
| | | MgSO$_4$.7H$_2$O | 0.5 g |
| | | ZnSO$_4$.7H$_2$O | 0.01 g |
| | | FeSO$_4$.7H$_2$O | 0.01 g |
| | | 1000 ml distilled water | |
| | | Bring to pH 6.5 with HCl | |
| Medium C | Production Medium: | same as B except no Lecithin algin | 1.0 g |
| Medium D | Production Medium: | same as C except: L-tryptophan (amino acid analog or substrate) | 2.0 g |
| | | L-phenylalanine (amino acid co-substrate) | 2.0 g |

I. Fermentation Production

A lyophilized tube of *Aspergillus alliaceus* was used to inoculate 18×175 mm agar slants containing 15 ml of medium A. After three weeks of growth at 27°, the spores from a slant tube were harvested by scraping into 6 ml 0.1% sodium lauryl sulfate. From the resulting spore suspension, 2 ml was used to inoculate 40 ml of medium B in a 250 ml three-baffle flask. The seed culture was incubated at 27° C. on a 220 rpm rotary shaker for 28 hours and then used to provide a 2.5 percent inoculum for 40 ml mediums C and D in 250 ml unbaffled flasks. Cultures in medium D were incubated on a 220 rpm rotary shaker at 27° for six days after which time the broth was assayed for compound 558. Compound 558 is formula I where $R_1$, $R_2$ and $R_3$ are each H and $R_4$ is $(CH_3)_2CH—CH_2—$. Following a growth period of 48 hours under the same conditions, ten flasks (400 ml) of the cultures in medium C were combined and centrifuged at 3000 rpm for 10 minutes. The supernatant was discarded and the mycelial pellet was washed three times with two volumes sterile 50 mM Mes pH 6.5. The cells were finally resuspended in the same buffer up to 200 ml total volume. Small scale incubations were set up in 25×150 mm tubes; 2 ml of the cell suspension was combined with 2 ml of the buffer containing the amino acid precursors. The exact conditions of the amino acid tube fermentations for the compound indicated are given in Table 1. After 24 hours on a 220 rpm rotary shaker at 27° C., the 4 ml broths were extracted with two successive 5 ml portions of ethyl acetate. The solvent was evaporated under a stream of nitrogen and the residue redissolved in methanol. HPLC analysis was used to determined contributions of compound 558 and related natural products.

II. Large Scale Washed Cell Fermentations

The seed culture in medium B was prepared as described in I and 10 ml was used to inoculate 400 ml of medium C in a two liter unbaffled Erlenmeyer flask. This culture was grown for 48 hours at 27° C. on a 220 rpm rotary shaker. The mycelia were harvested and washed as in I. In sterile 250 ml unbaffled flasks, 20 ml of the cell suspension was combined with 20 ml 50 mM Mes pH 6.5 which also contained selected amino acids. The exact conditions of the amino acid fermentations in flasks are given in Table 2. The flasks were placed on a 220 rpm rotary shaker at 27° C. After 36 hours, the whole broth was extracted twice with 1.5 volumes ethyl acetate which was then evaporated to dryness at reduced pressure. The residue was dissolved in methanol and subjected to HPLC analysis for compound 558. For large scale production of analogs of compound 558 duplicate fermentations were combined after the incubation period and extracted with ethyl acetate; this material was then used for isolation of the compounds.

III. HPLC Method

High performance liquid chromatography (HPLC) was used for quantitation of compound 558 in fermentation broths, initial discovery of potential analogs of compound 558 and final isolation of fermentation products. The apparatus used in this study consisted of a Beckman Model 342 liquid chromatography system equipped with a Model 165 UV detector and a Beckman 5 μm octyl, 4.6×250 mm reverse phase column. The column eluate was monitored at 235 nm and 210 nm. Analytical chromatography was performed isocratically using water/acetonitrile 60:40 at a flow rate of 1 ml/min. The capacity factors (k') for compound 558, the related natural products and selected analogs are listed in Table 3.

IV. Isolation of Compounds 328 and 329

The fermentation of D,L-trifluoromethyl-D,L-leucine produced two novel compounds as determined by high performance liquid chromatography (HPLC). The organic extract of 360 ml whole broth was concentrated to an oil under reduced pressure and redissolved in 4 ml methylene chloride. The resulting red solution was passed over a 25 ml silica gel column which had been equilibrated with methylene chloride. After washing with 1) 50 ml methylene chloride and 2) 50 ml ethyl acetate/methylene chloride (2:8), a 50 ml ethyl acetate eluate was collected and evaporated to dryness in vacuo. The residue was dissolved in 0.5 ml methylene chloride and applied, by repeated streaking, on a 2 mm silica gel chromatography plate (E. Merck 60F254 20×20 cm). Development in isopropanol/methylene chloride 6:94 produced two major UV positive bands: $R_f=0.25$ and $R_f=0.35$. After the bands were removed from the plate, the compounds were eluted from the silica with two 50 ml portions of ethyl acetate which was evaporated in vacuo. HPLC analysis revealed that Compound A and compounds 328 and 329 were eluted from the band at $R_f=0.25$. This material was dissolved in 700 μl MeOH and fractionated by preparative HPLC: Beckman C-8, 1×25 cm, 40% acetonitrile at 3 ml/min. compound 328 was eluted between 9.0 and 9.2 column volumes. Compound 329 was eluted between 11.2 and 11.4 column volumes. Isolation yields were 9.0 mg and 6.0 mg, respectively.

V. Isolation of Compounds 540 and 539

The fermentation of D,L-allylglycine (2-amino-4-pentenoic acid) produced two novel compounds as determined by HPLC analysis of the whole broth extract. The 400 ml ethyl acetate extract was evaporated to dryness in vacuo and redissolved in 4 ml methylene chloride. Column chromatography was performed as in IV. The ethyl acetate eluate was evaporated, redissolved in 700 μl methylene chloride and then subjected to preparative thin layer chromatography as in IV. The plate was developed 18 cm in isopropanol/methylene chloride 6:94, dried under a stream of nitrogen and redeveloped in the same solvent. Three UV positive bands were removed from the plate and eluted with ethyl acetate. A band at $R_f=0.60$ corresponded to 558. The material eluted from the two additional bands, $R_f=0.40$ and 0.51, was fractionated by HPLC as in IV. Compound 340 was eluted between 5.0 and 5.2 column volumes (TLC $R_f=0.40$). Compound 339 was eluted between 5.7 and 5.9 column volumes (TLC $R_f=0.51$). Isolation yields were 6.0 mg and 4.0 mg, respectively.

VI. Isolation of Compound 538

Fermentation of D,L-methylallyglycine (2-amino-4-methyl-4-pentenoic acid) produced a single novel component as determined by the HPLC method. The organic extract of the whole broth was evaporated to dryness and redissolved in 5 ml methylene chloride. Column chromatography was carried out as in IV. Preparative thin layer chromatography in isopropanol/methylene chloride 7:93 gave two major UV positive bands after a single development. The eluate from the band at $R_f=0.32$ was fractionated by HPLC. Compound 538 was eluted between 6.4 and 6.6 column volumes. 4.5 mg of product was isolated.

VII. Isolation of Compound 654

The fermentation of L-isoleucine with washed cells yielded a single novel compound as determined by HPLC. The ethyl acetate extract was evaporated and the residue subjected to a column chromatography as for the isolation of compound 328. A single development of the thin layer plate in isopropanol/methylene chloride 8:92 gave a major UV positive band at $R_f=0.5$ which contained compound A and the novel compound. Preparative HPLC as for the isolation of compound 328 was repeated twice in order to obtain 97% pure compound 654, which eluted between 9.8 and 10.0 column volumes 4.0 mg of the isoleucine analog was isolated

VIII. Isolation of Compound 656

Fermentation of L-norleucine produced a single novel component which eluted almost simultaneously with Compound A in the usual HPLC procedure. When the elution solvent was composed of water/acetonitrile/methanol 55:22.5:22.5, the two peaks were well separated. The isolation of compound 656 was almost identical to that of compound 654 except the two preparative HPLC steps involved isocratic elution with the solvent system noted above. Compound 656 eluted between 25.6 and 26.2 column volumes. 2.0 mg of the norleucine analog was isolated.

IX. Isolation of Compound 655

Fermentation of L-methionine with washed cells produced a single novel HPLC peak in the analysis of the whole broth organic extract. Material obtained from the usual silica gel, column chromatography step was dissolved in a minimal volume of methanol and subjected to two successive HPLC fractionation steps. The elution solvent consisted of water/acetonitrile/methanol 45:27.5:27.5 and compound 655 was eluted between 13.1 and 13.4 column volumes. 3.0 mg of the methionine analog was isolated.

X. Isolation of Compound 931

The fermentation of D,L-2-[3-cyclopentenyl]glycine with washed cells produced a single novel component as determined by HPLC. The ethyl acetate extract of the whole broth was evaporated and passed over a silica gel column in methylene chloride. The material obtained from the usual ethyl acetate elution was fractionated by HPLC using water/acetonitrile/methanol 60:37:3. The HPLC step was carried out twice; compound 931 was eluted between 14.1 and 14.4 column volumes. 1.2 mg of the cyclopentylglycine containing compound was isolated.

XI. Isolation of Compound 721

A single unknown HPLC peak was observed in the ethyl acetate extract of a washed cell fermentation of L-ethionine. The extract was evaporated in vacuo and the residue was redissolved in 4 ml methylene chloride. This solution was passed over silica gel (2×8 cm) which had been equilibrated with methylene chloride. The column was washed with 20 ml methylene chloride and then 20 ml ethyl acetate/methylene chloride (50:50). The unknown component was eluted with 25 ml ethyl acetate; fractions were assayed by TLC and HPLC. Following evaporation of the ethyl acetate, the sample was dissolved in 0.4 ml methanol and fractionated by the usual semi-preparative HPLC method (four 0.1 ml injections, 36% aqueous acetonitrile). The compound 721, eluted between 5.4 and 5.7 column volumes; the yield was 3.1 mg.

XII. Isolation of Compound 068

The fermentation of DL-α-cyclohexylglycine yielded a novel component which eluted from the HPLC column with a k' approximately twice the value of compound 558. The ethyl acetate solution was taken to dryness as usual and the resulting oil was dissolved in 5 ml methylene chloride. The material was fractionated by silica gel chromatography followed by reverse phase HPLC as in the isolation of compound 721. Using a solvent system composed of 43% aqueous acetonitrile, compound 068 eluted from the HPLC column after 10.2 column volumes; the yield was 5.4 mg.

XIII. Isolation of Compound 500

A single novel component, detected by HPLC, was produced from the fermentation of L-α-phenylglycine. The sample was extracted and taken through the silica gel chromatography as in the isolation of compound 068 and compound 721. The resulting material was dissolved in methanol and then fractionated by the usual reverse phase HPLC method, using 33% aqueous acetonitrile (four 0.1 ml injections). The compound eluted between 5.6 and 6.0 column volumes; the yield was 3.4 mg.

TABLE 1

| Tube Fermentations | | | |
|---|---|---|---|
| Amino Acid Analog, (mg/ml) | | Amino Acid cosubstrate, (mM) | |
| DL-6-fluorotryptophan | 0.5 | L-phenylalanine | 2 |
| DL-5-fluorotryptophan | 1.0 | L-phenylalanine | 2 |
| DL-7-azatryptophan | 0.5 | L-phenylalanine | 2 |
| DL-6-methyltryptophan | 1.0 | L-leucine | 10 |
| DL-5-methyltryptophan | 1.0 | L-leucine | 10 |
| DL-5-trifluoroleucine | 4.0 | L-phenylalanine | 20 |
| DL-3-methylallylglycine | 4.0 | L-phenylalanine | 20 |
| DL-allylglycine | 4.0 | L-phenylalanine | 20 |
| L-isoleucine | 4.0 | L-phenylalanine | 20 |
| L-norleucine | 4.0 | L-phenylalanine | 20 |
| L-methionine | 4.0 | L-tryptophan | 20 |
| DL-2-[3-cyclopentenyl]-glycine | 2.0 | L-tryptophan | 20 |
| L-ethionine | 2.0 | L-tryptophan | 15 |
| α-DL-cyclohexylglycine | 2.0 | L-tryptophan | 15 |
| α-L-phenylglycine | 2.0 | L-tryptophan | 15 |

TABLE 2

| Flask Fermentations | | | |
|---|---|---|---|
| Amino Acid Substrate (mg/ml) | Amino Acid Cosubstrate, (mM) | | Total Fermentation Volume (ml)* |
| DL-6-fluorotryptophan | 1.0 | none | 200 |
| DL-5-fluorotryptophan | 1.0 | none | 200 |
| DL-7-azatryptophan | 1.0 | none | 200 |
| DL-6-methyltryptophan | 1.0 | L-leucine | 20 | 360 |
| DL-5-methyltryptophan | 1.0 | L-leucine | 20 | 360 |
| DL-5-trifluoroleucine | 4.0 | L-phenylalanine | 20 | 360 |
| DL-3-methylallylglycine | 4.0 | L-phenylalanine | 20 | 360 |
| DL-allylglycine | 4.0 | L-phenylalanine | 20 | 240 |
| L-isoleucine | 4.0 | L-phenylalanine | 20 | 400 |
| L-norleucine | 4.0 | L-phenylalanine | 20 | 400 |
| L-methionine | 4.0 | L-tryptophan | 20 | 400 |
| DL-2-[3-cyclopentenyl]-glycine | 2.0 | L-tryptophan | 20 | 120 |
| L-ethionine | 4.0 | L-tryptophan | 20 | 400 |
| α-DL-cyclohexylglycine | 1.0 | L-tryptophan | 40 | 250 |
| α-L-phenylglycine | 4.0 | L-tryptophan, and L-phenylalanine | 20 6 | 500 |

*Fermentation volumes are multiples of the 40 ml production cultures.

TABLE 3

| Capacity Factors for High Performance Liquid Chromatography of Compound 558 and Related Compounds | |
|---|---|
| Compound | Capacity Factor (k') |
| 558 | 5.3 |
| 694 | 3.0 |
| 695 | 6.7 |
| 696 | 8.3 |
| 328 | 5.9 |
| 329 | 7.7 |
| 538 | 4.5 |
| 539 | 3.8 |
| 654 | 3.3 |
| 655 | 3.4 |
| 656 | 5.6 |
| 931 | 6.3 |
| 721 | 5.0 |
| 500 | 4.3 |
| 068 | 8.7 | k' = retention time (RT) of unknown compound-RT of an unretained compound/RT of the unretained compound.

Following are additional examples illustrating representative preparations. Temperature is in degrees Celsius unless otherwise noted.

EXAMPLE 1

Detection, Isolation and Purification of Compounds 842, 843 and 844

The resting-cell fermentation of the case organism with added 5-fluorotryptophan as described in Section II and Table 2 was extracted with ethyl acetate. After evaporation of the solvent under reduced pressure, the residue was taken up in methanol. Analysis of an aliquot of this solution by reverse-phase HPLC (Zorbax $C_{18}$ column, 4.6 mm×25 cm; eluent:acetonitrile-water 40:60; flow rate 2 ml/min at 40° C.; detection by UV at 254 nm) indicated the presences of four major UV-active components[1] rather than the two predicted from fermentation; one of the four peaks, as expected, corresponded and co-chromatographed with the major CCK antagonist of Formula A.

[1] k' values: compound 842: 3.5; compound 843: 8.4; compound 844: 11.9; for comparison on compound 558: 4.7.

The remainder of the methanol solution from above was fractionated on preparative scale by HPLC (Zorbax $C_{18}$, 1 inch×25 cm column; eluent:acetonitrile-water 45:55; flow rate 10 ml/min at 40° C.; detection by UV monitoring at 254 nm). After evaporation of the eluent from the appropriate fractions the solid residues were submitted to mass spectral analysis.

The three major components obtained were compound 842, 843 and 844.

EXAMPLE 2

Detection, Isolation and Purification of Compounds 856, 857 and 858

From the resting cell fermentation preparation described in Example 1 were isolated three further biosynthetic analogs of 558 and 694.

The whole broth was extracted with vigorous shaking with an equal volume of ethyl acetate; after separation of the phases, the organic layer was evaporated to dryness under reduced pressure.

The solid residue was dissolved in methanol and an aliquot of the solution used for analytical detection of new chemical entities[1] by reverse phase HPLC[2] (Zorbax $C_{18}$ column, 4.6 mm×25 cm; eluent:acetonitrile-water, 40:60; flow rate 2 ml/min at 40° C.; detection by UV at 254 nm). The three new major UV-active peaks were isolated on preparative scale using the remainder of the methanol solution. Conditions for the preparative isolation by reverse-phase HPLC: Zorbax $C_{18}$ column 1 inch×25 cm; eluent:acetonitrile-water 35:65; flow rate 10 ml/min at 40° C.; detection by UV at 254 nm.

These three purified compounds were analyzed by mass spectrometry and identified:
[1] Other than those detected and isolated as described in Example 1.
[2] k' values: compound 855: 9.4; compound 856: 2.6; compound 857: 5.6; for comparison compound 558: 4.7.

EXAMPLE 3

Isolation and Purification of Compound 841

From the resting cell fermentation of the test organism with added 7-aza-tryptophan was isolated, by chromatography, a new analog of compound 695.

This new derivative was detected by reversephase HPLC[1] (Zorbax $C_{18}$ column 4.6 mm×25 cm; eluent:acetonitrile-water, 40:60; flow rate: 2 ml/min at 40° C.; detection by UV absorption at 254 nm) in the ethyl acetate extract of the whole broth.

[1] k' value compound 841: 3.5; for comparison compound 558: 4.7.

After evaporation of the organic extract under reduced pressure, the residue was redissolved in a small amount of methanol and fractionated by preparative scale reverse-phase HPLC (Zorbax C18 column, 1 inch×25 cm; eluent:acetonitrile-water, 40:55; flow rate 10 ml/min; detection effected by UV monitoring at 254 nm). The fractions containing the eluted compound of interest (compound 841) were united, the solvent removed under reduced pressure with slight heating and the residue submitted to mass spectral analysis.

EXAMPLE 4

Detection and Isolation of Compound 845, 846 and 847

The resting-cell fermentation (section II & Table 2) in which 6-fluorotryptophan had been added, produced the three compounds 845, 846 and 847, which were identified as containing one, two or three-fluoro groups.

The ethyl acetate extract of the broth was analyzed by reverse-phase HPLC (Zorbax $C_{18}$ column 4.6 mm×25 cm eluent:acetronitrile-water 3:2, delivered at 2 ml/min and 40° C.); the three components of interest, compound 845, compound 846 and compound 847 all eluted after compound 558.[1]

[1] k' values; compound 845: 6.7; compound 846: 9.4; compound 847: 13.3; for comparison compound 558: 4.7.

Preparative scale isolation was achieved by reverse-phase HPLC (Zorbax $C_{18}$ 1 inch×25 cm column; eluent:acetonitrile-water 45:55, delivered at 10 ml/min and 40° C.). By monitoring the eluent at 254 nm, 2.56 AUFS, the three components were collected in distinct and separate zones. Characterization was accomplished by mass spectrometry after removal of the solvent by evaporation under reduced pressure.

EXAMPLE 5

Detection and Purification of Compound 880

The resting-cell fermentation prepared by the addition of 5-methyltryptophan (section II and table 2) was extracted with ethyl acetate. The organic layer was collected, evaporated to dryness under reduced pressure and redissolved in a small amount of methanol. Analysis by reverse-phase HPLC (Zorbax $C_{18}$ column 4.6 mm×25 cm eluent:acetonitrile-water 40:60, delivered at 2 ml/min and 40° C.) revealed the presence of one major biosynthetic analog as seen by UV absorption at 254 nm[1]. This component was obtained in pure form by preparative HPLC (Zorbax $C_{18}$ 1 inch × 1 ft column eluted with 45% aqueous acetonitrile at 10 ml/min and 40° C.). After chromatographic analysis of the fractions obtained, the appropriate positions were pooled, evaporated to dryness and the solid compound 880 obtained subjected to mass spectral analysis.

[1] k' values; compound 880: 11.0 for comparison compound 558: 4.7.

EXAMPLE 6

Detection and Purification of Compounds 881 and 882

The fermentation of the test organism with added 7-methyltryptophan (section II and table 2) was extracted with ethyl acetate. The organic layer was separated, evaporated to dryness and the solid residue redissolved in a small volume of methanol. Analysis by reverse-phase HPLC (Zorbax $C_{18}$ analytical column, 4.6 mm×25 cm, eluent:acetonitrile-water 40:60, delivered at 2 ml/min and 40° C.) revealed the presence of two major biosynthetic analogs as seen by UV absorption at 254 nm[1]. These components were obtained in pure form by preparative HPLC (Zorbax $C_{18}$ 1 inch×1 ft column eluted with 45% aqueous acetonitrile at 10 ml/min and 40° C.). After chromatographic analysis of the fractions obtained, the appropriate portions were pooled, evaporated to dryness and the solid compound 881 and 882 obtained were characterized by mass spectrometry.

[1] k' values: compound 881: 9.2; compound 882: 10.5 for comparison compound 558: 4.7.

The following data characterizes biosynthetic analogs of compound 558. All modifications are a result of the incorporation of a new amino acid in place of leucine. The characteristic fragmentation resulting from cleavage of the amino acid residue to give an ion at m/e 422 and ions corresponding to the indole moiety plus the incorporated amino acid are observed for each sample.

The low resolution mass spectra were recorded on a Finnigan-Mat 212 mass spectrometer in the electron impact mode (EI, 90 ev). Exact mass measurements were made on the same instrument at high resolution by the peak matching method using perfluorokerosene (PFK) as the internal standard. In each case the molecular ion was clearly observed and the following HR-MS values were obtained.

| STRUCTURE | FOUND | CALCULATED | FORMULA |
|---|---|---|---|
| 1 | 589.1939 | 589.1937 | $C_{31}H_{26}N_5O_4F_3$ |
| 2 | 589.1939 | 589.1937 | $C_{31}H_{26}N_5O_4F_3$ |
| 3 | 533.2065 | 533.2063 | $C_{31}H_{27}N_5O_4$ |
| 4 | 521.2060 | 521.2063 | $C_{30}H_{27}N_5O_4$ |
| 5 | 519.1904 | 519.1904 | $C_{30}H_{25}N_5O_4$ |
| 6 | 547.2216 | 547.2219 | $C_{32}H_{29}N_5O_4$ |
| 7 | 567.1942 | 567.1940 | $C_{31}H_{29}N_5O_4S$ |
| 8 | 561.2369 | 561.2376 | $C_{33}H_{32}N_5O_4$ |

Figure 1:
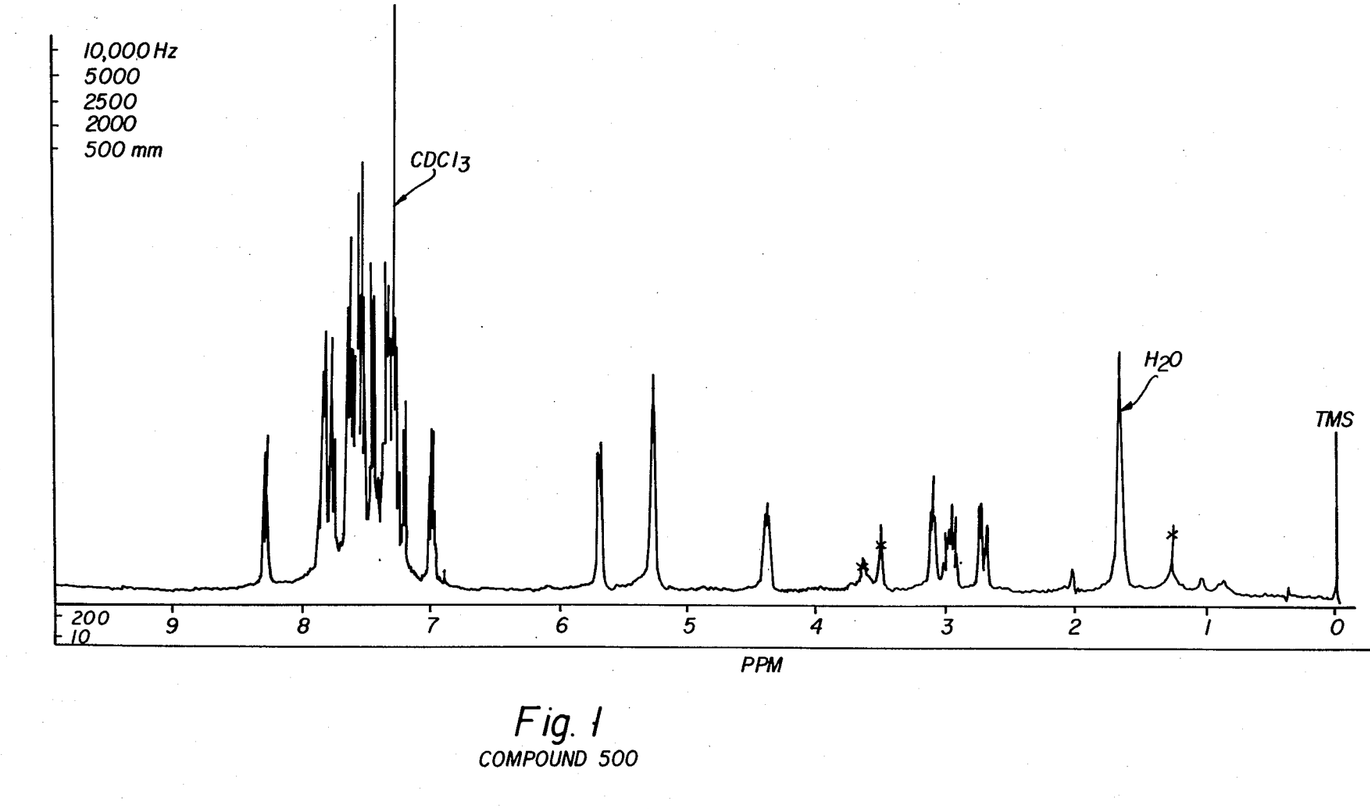
FIGS. 1–4 are NMR spectra (reduced) of Compound Numbers 500, 654, 655 and 656 respectively.
Figure 2:
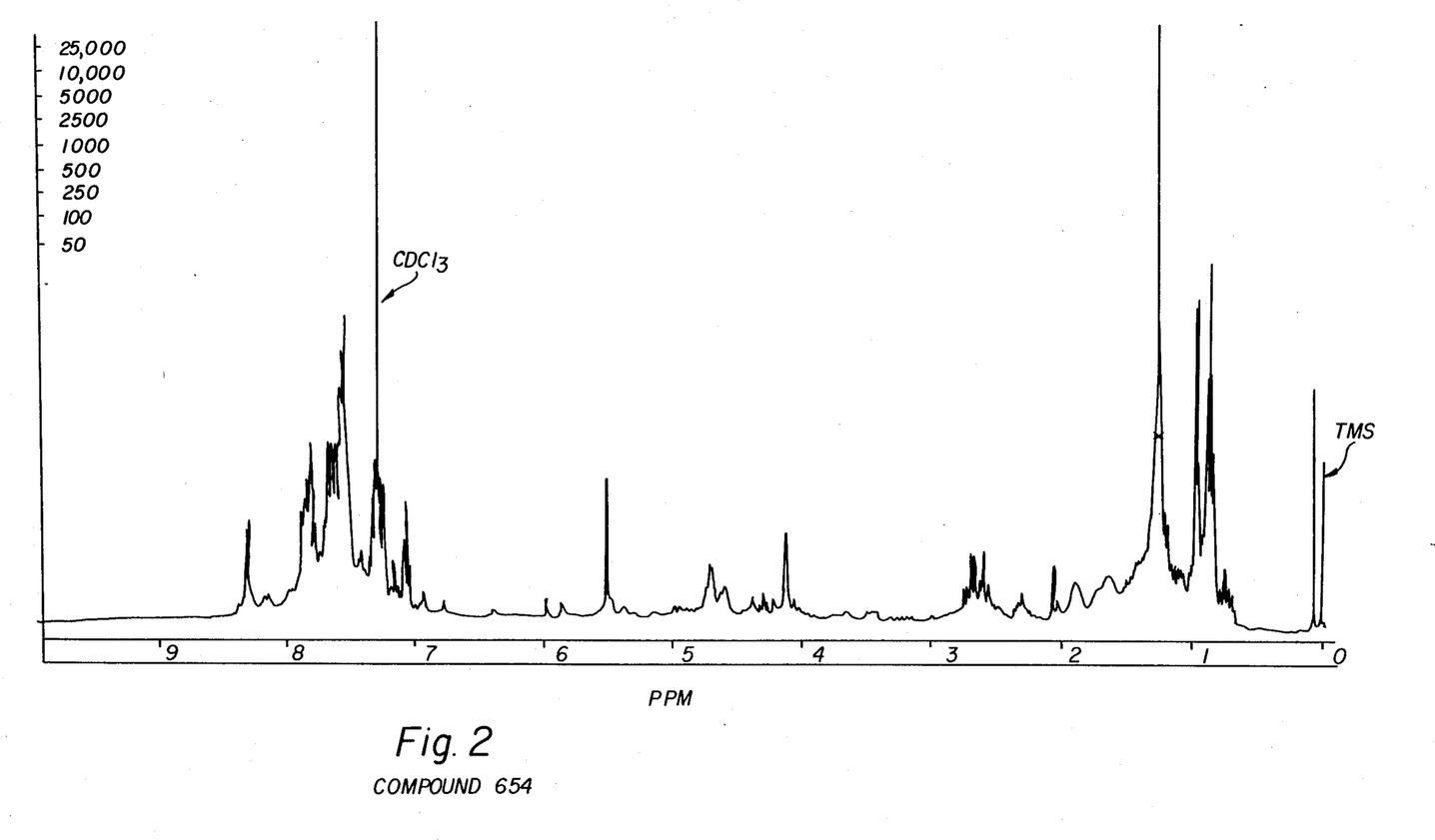
Figure 3:
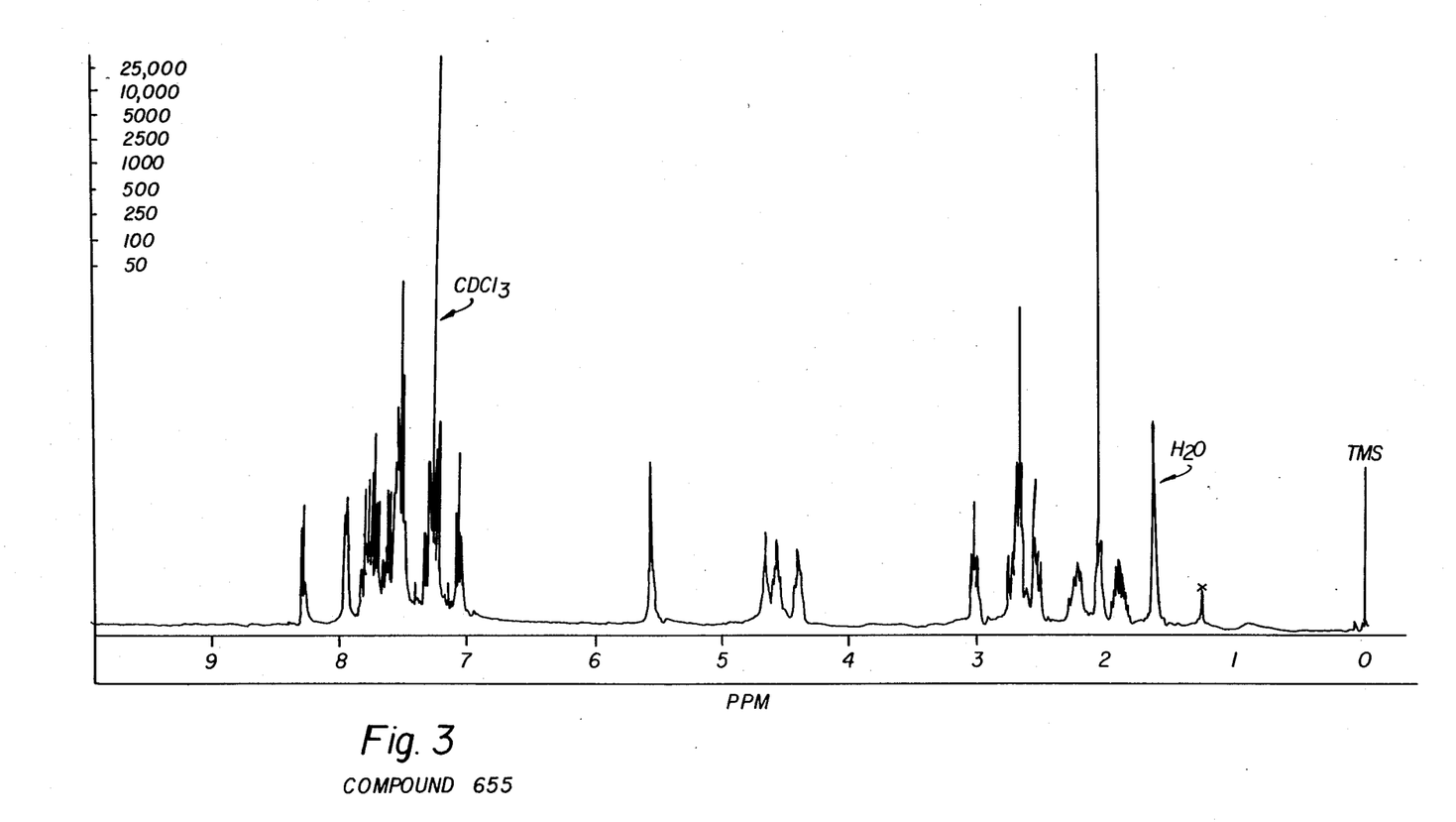
Figure 4:
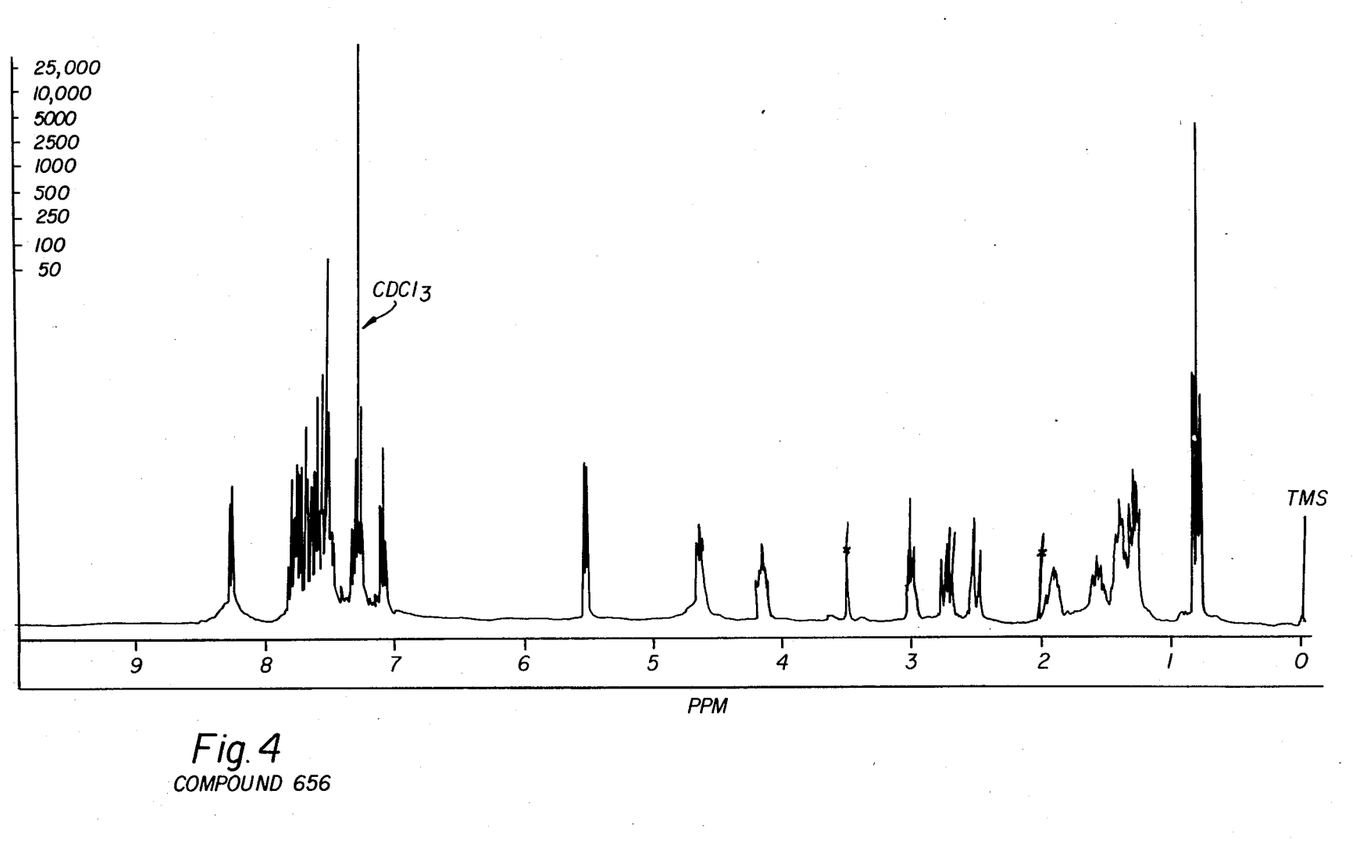

The following 4 biosynthetic analogs of compound 558 were characterized by MS as above (see data below) and by NMR. The NMR spectra were recorded in $CDCl_3$ at ambient room temperature on Varian SC-300 NMR spectrometer. Chemical shifts are shown in ppm relative to internal tetramethylsilane at zero ppm. A reducing photocopy of the spectrum of each compound is attached (see FIGS. 1–4).

| STRUCTURE | FOUND | CALCULATED | FORMULA |
|---|---|---|---|
| 9 | 555.1905 | 555.1906 | $C_{33}H_{25}N_5O_4$ |
| 10 (ms) (nmr) | 535* | | $C_{31}H_{29}N_5O_4$ |
| 11 | 535.2220 | 535.2220 | $C_{31}H_{29}N_5O_4$ |
| 12 | 553.1779 | 553.1784 | $C_{30}H_{27}N_5O_4S$ |

* = nominal molecular weight

The following structure and tabulation further identify Structures 1–12.

| STRUCTURE | COMPOUND NO. | Z (AMINO ACID RESIDUE) |
|---|---|---|
| 1 | 328 | 5-trifluoroleucine |
| 2 | 329 | 5-trifluoroleucine |
| 3 | 538 | L-2-amino-4-methyl-4-pentenoic acid |
| 4 | 539 | L-2-amino pentanoic acid |
| 5 | 540 | L-2-amino-4-pentenoic acid |
| 6 | 931 | cyclopentylglycine |
| 7 | 721 | L-ethionine |
| 8 | 068 | L-2-cyclohexylglycine |
| 9 | 500 | L-2-phenylglycine |
| 10 | 654 | L-isoleucine |
| 11 | 656 | L-norleucine |
| 12 | 655 | L-methionine |

The following data characterizes other biosynthetic analogs of compound 558 which were isolated. The low resolution mass spectra were record on a Finnigan-Mat 212 mass spectrometer in the electron impact mode (EI, 90 ev). Exact mass measurements were made on the same instrument at high resolution by the peak matching method using perfluorokerosene (PFK) as the internal standard. Ih each case the molecular ion was clearly observed and the following HR-MS values were obtained.

| COMPOUND NO. | FOUND | CALCULATED | FORMULA |
|---|---|---|---|
| 841 | 407.1382 | 407.1382 | $C_{24}H_{17}N_5O_2$ |
| 842 | 458.1185 | 458.1190 | $C_{25}H_{16}N_4O_3F_2$ |
| 843 | 571.2031 | 571.2031 | $C_{32}H_{27}N_5O_4F_2$ |
| 844 | 589.1930 | 589.1937 | $C_{32}H_{26}N_5O_4F_3$ |
| 845 | 553.2125 | 553.2125 | $C_{31}H_{28}N_5O_4F$ |
| 846 | 571.2031 | 571.2031 | $C_{31}H_{27}N_5O_4F_2$ |
| 847 | 589.1937 | 589.1937 | $C_{31}H_{26}N_5O_4F_3$ |
| 855 | 571* | | $C_{31}H_{27}N_5O_4F_2$ |
| 856 | 440* | | $C_{25}H_{17}N_4O_3F$ |
| 857 | 476* | | $C_{25}H_{15}N_4O_3F_3$ |
| 880 | 563.2532 | 563.2532 | $C_{33}H_{33}N_5O_4$ |
| 881 | 420.1580 | 420.1586 | $C_{26}H_{20}N_4O_2$ |
| 882 | 549.2376 | 549.2376 | $C_{32}H_{31}N_5O_4$ |

* = Nominal molecular weight

The following formula and tabulation further identify the above listed compounds. Pancreatic CCK inhibition data is also provided; the assay used is that disclosed in said European Patent Application No. 0,116,150.

B

| Analog Used | Compound Number | Isolated Derivative of Compound Number | B-Substituents | Pancreatic CCK IC$_{50}$ ($\mu$g/ml) |
|---|---|---|---|---|
| 5-fluoro-Trp | 843 | 558: | $R_1=R_3=F$ | 1.6 |
| ↓ | 844 | 558: | $R_1=R_2=R_3=F$ | 0.8 |
|  | 855 | 558: | $R_1=R_2=F$ | 0.6 |
|  | 842 | 694: | $R_1=R_3=F$ | 11.1 |
|  | 856 | 694: | $R_1=F$ | 13.2 |
|  | 857 | 694: | $R_1=R_2=R_3=F$ | 1.2 |
| 6-fluoro-Trp | 845 | 558: | $R_3=F$ | 0.8 |
| ↓ | 846 | 558: | $R_2=R_3=F$ | 3.3 |
|  | 847 | 558: | $R_1=R_2=R_3=F$ | 10.9 |
| 7-aza-Trp | 841 | 695: | 7-aza-indole | 12.2 |
| 5-methyl-Trp | 880 | 558: | $R_2=R_3=CH_3$ | — |
| 7-methyl-Trp | 881 | 695: | $R_1=CH_3$ | — |
| ↓ | 882 | 558: | $R_1=CH_3$ | — |

Following are structures of some compounds, as indicated:

Compound 558

Compound 753

Compound 696

Compound 695

Compound 694

The following table contains information identifying other compounds of the present invention and pancrease CCK inhibition data (European Patent Application Assay).

TABLE

| Compound No. | Leucine Analog | Compound 558 Derivative Where R₄ is | Pancreatic CCK IC$_{50}$ (uM) |
|---|---|---|---|
| 328 | F$_3$C, H$_3$C, H, CO$_2^-$, NH$_2$ | F$_3$C, H$_3$C, H | 1.0 |
| 329 | | H$_3$C, F$_3$C, H | 1.0 |
| 538 | H$_3$C, (CH$_3$)C=CH-, H, CO$_2^-$, NH$_2$ | H$_3$C, (CH$_3$)C=CH- | 3.3 |
| 540 | H, (CH$_3$)C=CH-, H, CO$_2^-$, NH$_2$ | H | 7.6 |
| 539 | | H$_3$C, H, H | 11.9 |
| 531 | cyclopentenyl, H, CO$_2^-$, NH$_2$ | cyclopentenyl | 2.2 |
| 654 | L-Isoleucine | H$_3$C, H$_3$C- | 5.9 |
| 656 | L-Norleucine | H$_3$C- | 2.5 |
| 655 | L-Methionine | H$_3$C-S- | 4.1 |
| 721 | L-Ethionine | CH$_3$CH$_2$S- | 1.5 |
| 500 | α-L-Phenylglycine | phenyl | 20.0 |
| 068 | α-DL-Cyclohexylglycine | cyclohexyl | 0.6 |

We claim:

1. A compound having the formula or or and pharmaceutically acceptable salts thereof wherein $R_1$, $R_2$, and $R_3$ are independently selected from H, F, and $CH_3$ and $R_4$ is selected from phenyl, cyclohexyl, cyclopentyl, $(CH_3)_2CH\text{---}CH_2\text{---}$, $(CF_3)(CH_3)CH\text{---}CH_2\text{---}$, $CH_2\text{=}C(CH_3)CH_2\text{---}$, $CH_2\text{=}CHCH_2\text{---}$, $CH_3\text{---}CH_2\text{---}CH_2\text{---}$, $CH_3\text{---}CH_2\text{---}(CH_3)CH$, $CH_3(CH_2)_3\text{---}$, $CH_3\text{---}S\text{---}(CH_2)_2\text{---}$, and $CH_3\text{---}CH_2\text{---}CH_2\text{---}S\text{---}CH_2\text{---}$ with the proviso that (i) $R_1$, $R_2$ and $R_3$ are all H only when $R_4$ is other than $(CH_3)_2\text{---}CH\text{---}CH_2$ and (ii) in structure II $R_1$, $R_2$ and $R_3$ are not all H.

2. Compound of claim 1, Formula I.

3. Compound of claim 2 wherein each of $R_1$, $R_2$ and $R_3$ is H.

4. Compound of claim 3 wherein $R_4$ is

5. Compound of claim 1, Formula II.

6. Compound of claim 1, Formula III.

7. A mixture of compounds of claim 1, Formula I.

8. A mixture of compounds of claim 1, Formula II.

9. A pharmaceutical composition for effecting cholecystokinin inhibition containing a therapeutically effective amount of a compound of claim 1 and a pharmaceutically acceptable carrier.

* * * * *